United States Patent
Wilking

Patent Number: 5,698,217
Date of Patent: Dec. 16, 1997

[54] TRANSDERMAL DRUG DELIVERY DEVICE CONTAINING A DESICCANT

[75] Inventor: Shari L. Wilking, Minnesota, Minn.

[73] Assignee: Minnesota Mining and Manufacturing Company, St. Paul, Minn.

[21] Appl. No.: 454,919

[22] Filed: May 31, 1995

[51] Int. Cl.$^6$ .............................. A61K 37/00; B65D 81/26
[52] U.S. Cl. .................. 424/448; 424/449; 206/204; 206/440; 206/828
[58] Field of Search ......................... 424/448, 449; 206/204, 440, 828

[56] References Cited

U.S. PATENT DOCUMENTS

| | | | |
|---|---|---|---|
| Re. 24,906 | 12/1960 | Ulrich | 206/59 |
| 4,036,360 | 7/1977 | Deffeyes | 206/204 |
| 4,732,808 | 3/1988 | Krampe et al. | 428/355 |
| 4,814,173 | 3/1989 | Song et al. | 424/444 |
| 4,820,525 | 4/1989 | Leonard et al. | 424/486 |
| 4,832,953 | 5/1989 | Campbell et al. | 424/448 |
| 4,834,979 | 5/1989 | Gale | 424/448 |
| 5,008,110 | 4/1991 | Benecke et al. | 424/448 |
| 5,077,104 | 12/1991 | Hunt et al. | 428/34.3 |
| 5,223,261 | 6/1993 | Nelson et al. | 424/443 |
| 5,232,702 | 8/1993 | Pfister et al. | 424/448 |
| 5,310,559 | 5/1994 | Shah et al. | 424/448 |
| 5,336,210 | 8/1994 | Hidaka et al. | 604/307 |
| 5,370,924 | 12/1994 | Kochinke | 428/224 |

FOREIGN PATENT DOCUMENTS

| | | |
|---|---|---|
| 260452 | 3/1988 | European Pat. Off. . |
| 556158 | 8/1993 | European Pat. Off. . |
| 4210711 | 5/1993 | Germany . |
| 92/12004 | 7/1992 | WIPO . |
| 94/25263 | 11/1994 | WIPO . |

*Primary Examiner*—Edward J. Webman
*Attorney, Agent, or Firm*—Gary L. Griswold; Walter N. Kirn; Ted K. Ringsred

[57] ABSTRACT

A transdermal drug delivery device involving a carrier containing a dissolved drug. The device also involves a desiccant package that is inert to the carrier, permeable to water vapor, and defines a desiccant compartment containing a desiccant. The device also involves water vapor impermeable product package that contains the carrier and the desiccant package.

7 Claims, 1 Drawing Sheet

TRANSDERMAL DRUG DELIVERY DEVICE CONTAINING A DESICCANT

BACKGROUND OF THE INVENTION

1. Technical Field

This invention relates to transdermal drug delivery devices. In another aspect this invention relates to devices for delivering drugs to and/or across the skin. In yet another aspect, this invention relates to methods of inhibiting precipitation of drugs in a transdermal drug delivery device.

2. Description of the Related Art

Transdermal drug delivery can provide significant advantages as compared to other routes of drug delivery. For example in contrast to injection it is non-invasive. In contrast to oral administration it avoids first pass metabolism and gastrointestinal absorption difficulties caused by gastrointestinal pH or enzymatic activity. Transdermal administration is becoming increasingly useful with continued development of systems suitable for carrying and releasing drugs to the skin and systems for optimizing the rate of percutaneous absorption. Because of the above noted advantages of transdermal administration many drugs are being considered for transdermal delivery. Commercially available transdermal systems include ones that deliver steroid hormones (e.g., estradiol for treatment of symptoms of menopause), nicotine (for smoking cessation), nitroglycerine (for angina), scopolamine (for motion sickness), and fentanyl (a narcotic analgesic for treatment of pain).

Devices that have found use include adhesive matrix type devices wherein the drug is dissolved or dispersed in an adhesive matrix that is applied to the skin in order to deliver the drug. Reservoir type devices have also found use. The drug is dissolved or dispersed in a reservoir (e.g., a polymeric or liquid matrix sometimes involving a membrane that controls the rate of drug release from the device) and the reservoir is held in place on the skin by a pressure sensitive skin adhesive.

In devices wherein the drug is intended to be dissolved in an adhesive matrix or some other carrier, unexpected precipitation of the drug can cause the rate of drug delivery to decrease as the drug crystallizes. Such instability can render the product unsuitable for commercial use, which often involves storage of the product for periods of up to several years. It is therefore very desirable in certain transdermal drug delivery devices that the drug remain dissolved.

SUMMARY OF THE INVENTION

The several components of a transdermal drug delivery device generally contain at least small amounts of water, which might not be intentionally incorporated but could be incidentally present, e.g., as a result of method of manufacture or exposure to ambient moisture during manufacture or storage. Certain drugs tend to interact with this water and form relatively insoluble forms (e.g., solid hydrates). Consequently certain transdermal delivery devices involving dissolved drugs have shown a tendency to exhibit precipitation of the drug during storage. This problem is at least in part attributable to formation hydrate forms of the drug. Accordingly this invention provides a method of inhibiting precipitation of a drug in the carrier of a transdermal drug delivery device, comprising the steps of:

(i) providing a non-aqueous carrier comprising a dissolved drug that forms a solid hydrate when exposed to water vapor;

(ii) providing a desiccant package permeable to water vapor and defining a desiccant compartment containing a desiccant; and (iii) placing said desiccant package and said carrier within a substantially sealed water vapor impermeable product package.

This invention also provides a transdermal drug delivery device comprising: a non-aqueous carrier comprising a dissolved drug that forms a solid hydrate when exposed to water vapor; a desiccant package permeable to water vapor and defining a desiccant compartment containing a desiccant; and a water vapor impermeable product package, wherein the carrier and the desiccant package are contained within the product package.

Through the use of a desiccant this invention lessens or avoids precipitation (e.g., crystallization) in transdermal drug delivery devices containing drugs that form hydrate forms upon exposure to water. The desiccant system can be made small, thin, and flexible, allowing incorporation into a flexible unit-dose transdermal drug delivery system product package without adversely affecting the appearance or shape of the product package.

DETAILED DESCRIPTION OF THE INVENTION

Figure 1:
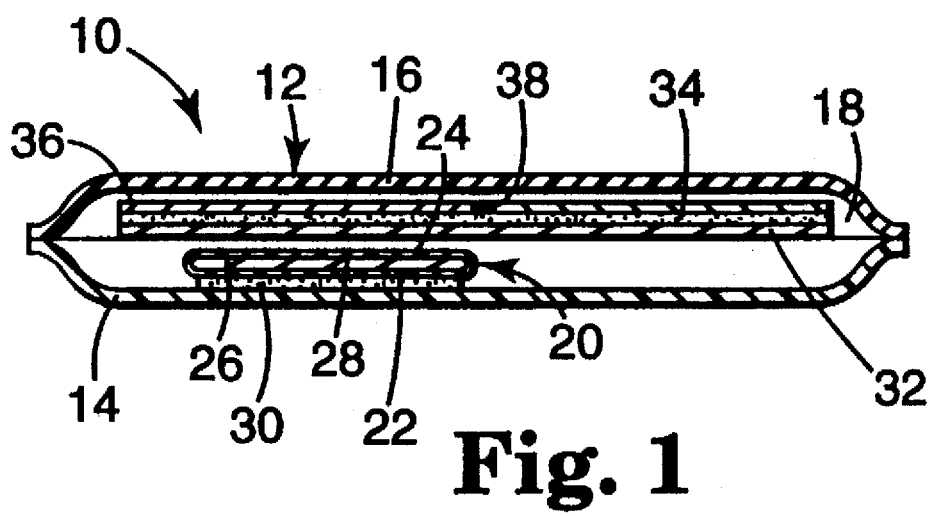
FIG. 1 is cross sectional view of a transdermal drug delivery device of the invention.

A transdermal drug delivery device of the invention comprises a carrier, preferably a non-aqueous carrier, suitable for use in a transdermal drug delivery device. As used herein the term "non-aqueous carrier" refers to a substantially water free carrier that contains only small amounts of water, for example less than about one to five percent by weight of water as may be incidentally present in materials of construction that have not been dried prior to use. Examples of suitable carriers include pressure sensitive skin adhesives (e.g., those disclosed in U.S. Pat. Nos. RE 24,906 (Ulrich), 4,732,808 (Krampe), and 5,232,702 (Pfister)), non-adhesive polymeric matrices (e.g., those disclosed in U.S. Pat. No. 4,814,173 (Song)), and other reservoir systems (e.g., those disclosed in U.S. Pat. Nos. 4,834,979 (Gale), 4,820,525 (Leonard), and 5,310,559 (Shah)). A particularly preferred carrier is an acrylate pressure sensitive adhesive such as that disclosed, e.g., in U.S. Pat. No. 5,223,261 (Nelson et al.) and commonly assigned copending application Ser. No. 08/305,833. Depending on the particular carrier, suitable adjuvants and excipients can be included, e.g., in order to dissolve the drug or other excipients, or to enhance the rate of skin penetration. Suitable adjuvants and excipients that may be used include $C_8$–$C_{22}$ fatty acids such as isostearic acid, octanoic acid, and oleic acid, $C_8$–$C_{22}$ fatty alcohols such as oleyl alcohol and lauryl alcohol, lower alkyl esters of $C_8$–$C_{22}$ fatty acids such as ethyl oleate, isopropyl myristate, butyl stearate, and methyl laurate, di(lower) alkyl esters of $C_6$–$C_8$ diacids such as diisopropyl adipate, monoglycerides of $C_8$–$C_{22}$ fatty acids such as glyceryl monolaurate, tetrahydrofurfuryl alcohol polyethylene glycol ether, polyethylene glycol, propylene glycol, 2-(2-ethoxyethoxy)ethanol, diethylene glycol monomethyl ether, N,N-dimethyldodecylamine-N-oxide, and combinations of the foregoing. Alkylaryl ethers of polyethylene oxide, polyethylene oxide monomethyl ethers, and polyethylene oxide dimethyl ethers are also suitable, as are solubilizers such as dimethyl sulfoxide, glycerol, ethanol, ethyl acetate, acetoacetic ester, N-methyl pyrrolidone, and isopropyl alcohol.

In the preferred acrylate pressure sensitive adhesive carrier, preferred adjuvants include glyceryl monolaurate, diethylene glycol monomethyl ether, tetrahydrofurfuryl alcohol polyethylene glycol ether, diisopropyl adipate, propylene glycol, isopropyl myristate, ethyl oleate, methyl laurate, 2-(2-ethoxyethoxy)ethanol, and oleyl alcohol.

Generally the carrier will have a surface that is intended to be applied to the skin. The area of this surface is variable but is generally about 1 cm$^2$ to about 25 cm$^2$.

The carrier contains a dissolved drug that forms a solid hydrate when exposed to water vapor ("solid hydrate" as used herein refers to a material that is solid, for example crystalline, at 0° C.). The carrier is preferably substantially free of undissolved drug.

Generally solid hydrates are less soluble than the anhydrous form in non-aqueous media. In the practice of the invention the drug is preferably one that, when exposed to water vapor, forms a hydrate crystal form that is less soluble than the anhydrous form of the drug in a non-aqueous transdermal carrier. Certain steroid hormones, including estradiol, are known to form such hydrates upon exposure to water. Other drugs that have been said to form hydrates include scopolamine, nicotine, secoverine, and benztropine.

A device of the invention also comprises a desiccant package. Suitable desiccant packages include those that are inert to the carrier (i.e., those that neither react chemically with, nor swell with, nor otherwise absorb components of the carrier). Preferably the desiccant package is free of components (e.g., plasticizers such as phthalates) that can be leached from the desiccant package by the components of the carrier. The desiccant package is permeable to water vapor in order that the desiccant inside may take up any water vapor that might be present in or become introduced into the product package. Suitable materials of construction of a desiccant package for use in connection with a particular carrier can be selected by those skilled in the art. Representative water vapor permeable materials include polyethylene, polypropylene, ethylene/vinyl acetate, polyethylene terephthalate, paper, coated paper, and perforated sheet materials including perforated laminates such as a perforated metallized polyethylene terephthalate/paper laminate. Other suitable materials that can be used along with a water vapor permeable material include impermeable materials such as styrene/butadiene copolymer films, e.g., OPTICITE SQZ label film.

The desiccant package can be configured in any manner that defines a desiccant compartment. It is preferred that the desiccant package define a closed desiccant compartment and be thin, flat, and flexible in order that it can be inconspicuous when incorporated into a transdermal drug delivery device. In a preferred embodiment the desiccant package comprises a base sheet and a coextensive cover sheet sealed together around the periphery (e.g., by an adhesive, by heat sealing, or by any other suitable sealing method). The desiccant compartment is formed by the two sheets and the peripheral seals therebetween. The base sheet, the cover sheet, or both are permeable to water vapor. In a preferred embodiment the base sheet is a water vapor impermeable styrene/butadiene copolymer film (OPTICITE SQZ label film, Dow Corning), the cover sheet is a metallized polyethylene terephthalate/paper laminate (Schwartz Paper Company), and the sheets are sealed around their periphery by an adhesive bond. In yet a further preferred embodiment the desiccant package is immobilized within the transdermal drug delivery device of the invention.

The desiccant compartment contains a desiccant in order to absorb, adsorb, react with, or otherwise remove water, such as any water that may be incidentally present in the various components of the device. Materials known for use as desiccants include barium oxide, calcium chloride, calcium oxide, calcium sulfate, lithium chloride, perchlorates such as lithium, barium, or magnesium perchlorate, phosphorous pentoxide, alumina, silica gel, and zeolite molecular sieve. The desiccant can be used in any amount that is effective to absorb water vapor from the product package over the shelf life of the product. The amount of desiccant that constitutes an effective desiccating amount depends on several factors readily assessed by those skilled in the art, including the amount of water present in the components of the device, the capacity of the selected desiccant to take up water, and the presentation of the desiccant relative to the components of the device containing water.

The desiccant preferably does not absorb, react with, or otherwise adversely affect the drug, other excipients or adjuvants, or packaging materials that are used in the transdermal device. Suitability and compatibility of particular desiccants for use in a particular transdermal device can be readily determined by those skilled in the art considering the particular components that are to be used. For example, while the most common desiccant system currently used by the U.S. pharmaceutical industry involves silica gel, silica gel has been found to adsorb materials such as fatty acid esters that are commonly used as excipients in transdermal drug delivery. Change in excipient level over time can cause unstable product performance. Thus silica gel is not preferred for use in devices where fatty acid ester content is critical to product performance.

Desiccants that selectively remove water vapor are preferred. Natural and synthetic zeolite molecular sieves, including zeolite A, e.g., 3 A, 4 A, and 5 A molecular sieve, are most preferred. A zeolite molecular sieve desiccant is preferably powdered, e.g., to a mesh size of about 30–40.

A device of the invention further comprises a product package, which contains the carrier and the desiccant package and isolates them from the ambient environment. The product package is substantially impermeable to water vapor. It can be configured in any manner that defines a sealed product-receiving space. In a preferred embodiment the product package comprises a base sheet and a coextensive cover sheet sealed together around the periphery (e.g., by an adhesive, by heat sealing, or by any other suitable sealing method), whereby the product receiving space is defined by the two sheets and the peripheral seals therebetween. Suitable materials for use as the product package include cold-sealable laminates such as paper/foil/polyethylene, paper/foil/vinyl primer, or paper/foil/polyvinyldichloride, flood coated or pattern coated with natural or synthetic adhesive, and heat sealable film laminates involving paper or foil and high, medium, low, or linear low density polyethylene, polypropylenes, or polyesters.

In a preferred embodiment the desiccant package is immobilized within the product package, e.g., by sealing into the peripheral seal about the base sheet and cover sheet or by means of an adhesive, such as a pressure sensitive adhesive layer, between the desiccant package and the inner surface of the product package.

Generally in a device of the invention the carrier is part of a laminate structure wherein the carrier is borne upon a backing. Suitable backings include flexible backing materials used for pressure sensitive adhesive tapes, such as polyethylene, particularly low density polyethylene, linear low density polyethylene, high density polyethylene, polyester such as polyethylene terephthalate, randomly oriented nylon fibers, polypropylene, ethylene:vinyl acetate copolymers, polyurethane, rayon, and the like. Backings that are layered, such as polyethylene-polyester-aluminum-polyethylene composites, are also suitable.

The surface of the carrier not covered by the backing is generally covered by a release liner, which can be removed from the laminate to allow application and adhesion to the skin. Suitable release liners include conventional release liners comprising a sheet material such as a polyester web, a polyethylene web, or a polystyrene web, or a polyethylene-coated paper, coated with a suitable fluoropolymer or silicone based coating. Suitable differential release liners include conventional differential release liners comprising a sheet material such as a polyester web, a polyethylene web, or a polystyrene web, or a polyethylene-coated paper, coated on both surfaces with suitable fluoropolymer or silicone based coatings. Referring now to the Drawing, device 10 shown in FIG. 1 comprises product package 12 comprising substantially coextensive water vapor impermeable sheets 14 and 16 sealed around their periphery to define product receiving space 18. Like the product package, desiccant package 20 comprises substantially coextensive sheets 22 and 24, at least one of which is permeable to water vapor, sealed around their periphery. Desiccant receiving space 26 contains desiccant 28. Sheet 22 bears layer 30 of pressure sensitive adhesive. The pressure sensitive adhesive layer adheres also to sheet 14 immobilizing the desiccant package within the product package.

Product receiving space 18 also contains a laminate comprising backing 32, carrier 34, and release liner 36. Backing 32 bears carrier 34, which in the illustrated embodiment is a pressure sensitive adhesive matrix comprising a drug. Release liner 36 covers carrier 34 and can be readily removed by bending the laminate such that the release liner splits at point 38 where the release liner is cut.

The components of a device of the invention (e.g., the various packaging materials, adhesives, drugs, desiccants, and other components of transdermal carriers including adjuvants and excipients) are readily available from commercial sources and/or readily prepared by those skilled in the art using well known methodology. For example a pressure sensitive adhesive coated desiccant package containing 4 A molecular sieve is available from Multiform Desiccants (Buffalo, N.Y.). A device of the invention can be prepared by assembling the several components into a transdermal drug delivery device using coating, laminating, and sealing methods well known to those skilled in the art and disclosed, e.g., in U.S. Pat. Nos. 5,223,261 (Nelson et al.), 5,008,110 (Benecke), 5,370,924 (Kochinke), and 5,077,104 (Hunt), WO 92/12004 (Cullen at al.), and EP 556 158 (Rudella), all incorporated herein by reference.

A device of the invention can be used in any application where transdermal drug delivery is useful, e.g., in treatment of symptoms of menopause by administration of estradiol, and is particularly useful in connection with transdermal delivery of drugs that when exposed to water form a hydrate that precipitates from the carrier. In use the carrier is removed from the product package and applied to a patient. The carrier is allowed to remain in place for a time sufficient to achieve and/or maintain a therapeutically effective blood level of the drug. The mount of drag and duration of treatment can be selected by those skilled in the art considering the particular drug to be administered and the particular intended therapeutic effect.

The following Examples illustrate but do not limit the invention.

EXAMPLE 1

A Ross Mixer was charged with adhesive copolymer solution [78,033 g of 75/5/20 isooctyl acrylate/acrylamide/vinyl acetate 24.5% solids in 90/10 w/w methanol/ethyl acetate prepared generally as described in U.S. Pat. No. 5,223,261 (Nelson et al.)], estradiol, USP (750 g), glyceryl monolaurate (921 g), isopropyl myristate, NF (2,632 g), and ethyl oleate, NF (3,684 g). The mixer lid was clamped in place and the ports were sealed to minimize loss of solvent during mixing. The mixer blade was set at a speed of 24.5 rpm and the contents were mixed for about 22 hours. The resulting formulation was transferred using nitrogen pressure (3-5 psi, 211-351 g/cm$^2$) to polyethylene containers. The formulation was die coated onto a one side silicone coated polyester release liner (2 mil, 0.051 mm). The coated release liner was oven dried at 52° C. for 1.25 minutes, at 107° C. for 1.25 minutes and at 121° C. for 1.25 minutes. This material was then laminated to two side corona treated low density polyethylene film (3 mil, 0.076 mm) to provide rollstock containing 1.6 mg of estradiol per 5.14 cm$^2$. A portion of the rollstock was die cut into patches (5.14 cm$^2$). Each patch, along with approximately 30 mg of 3 A molecular sieve in pellet form, was packaged in a heat sealed multilaminate pouch (exterior to interior: bleached Kraft paper, low density polyethylene, aluminum foil, low density polyethylene).

Comparative Example 1

A portion of the rollstock prepared in Example 1 was die cut into patches (5.14 cm$^2$). Each patch was packaged in a heat sealed multilaminate pouch identical to that used in Example 1.

EXAMPLES 2-5

Four additional lots of rollstock were prepared using the general method of Example 1 except that the rollstock of Example 3 was formulated to contain approximately 1% more isopropyl myristate and that of Example 5 was formulated to contain approximately 1% less isopropyl myristate as compared to the formulation of Example 1. A portion of each rollstock was die cut into patches (5.14 cm$^2$). Each patch, along with approximately 30 mg of 3 A molecular sieve in pellet form, was packaged in a heat sealed multilaminate pouch (exterior to interior: bleached Kraft paper, low density polyethylene, aluminum foil, low density polyethylene).

Comparative Examples 2-5

A portion of the rollstock prepared in each of Examples 2-5 was die cut into patches (5.14 cm$^2$). Each patch was packaged in a heat sealed multilaminate pouch identical to those used in Examples 2-5.

All 10 lots of the packaged patches were then stored in a stability chamber at 40° C. and 75% relative humidity. After 3 months all 10 lots were examined for the presence of crystals. Crystals were present in all five of the lots that had been packaged without desiccant. There were no crystals observed in any of the five lots that had been packaged with desiccant. The release rate of estradiol from the patches was determined using the test method described below. The results of the release rate test are shown in Table 1 where the value indicates the percent of estradiol released after 180 minutes in the dissolution apparatus, each value is the average of determinations for 3 separate patches, and the absence of an entry indicates that the test was not run at that time point.

Estradiol Transdermal Patch Release Rate

This method describes the dissolution test procedure to evaluate in-vitro release characteristics of estradiol transdermal delivery patches.

The method uses a Hanson Dissolution Apparatus with the dissolution medium temperature set at 32° C. and the paddle speed set at 75 rpm.

Each patch (5 cm², die cut to size if necessary) is affixed with double coated tape to the center of the long axis of a plexiglass cylinder (3.8 cm wide by 6 cm high with a USP basket shaft connector centered at one end) so that the release liner is facing upward (The patch backing is in direct contact with the double coated tape.) and the long axis of the tape patch is on the equator of the plexiglass cylinder.

A dissolution flask (a 5.08 cm inside diameter cylinder) is partially filled with exactly 150 mL of dissolution medium (prepared by placing 300 mL of 200 proof ethanol in a 1,000 mL volumetric flask then diluting to volume with water, HPLC grade, deaerated). The flask is covered to minimize loss by evaporation then allowed to equilibrate at 32° C.

The release liner is removed from the patch. The plexiglass cylinder is mounted on the basket shaft then centered in the dissolution flask such that its sides are equidistant with the flask walls and the bottom of the cylinder is 0.5 cm above the bottom of the flask.

At specified time points a 2.0 mL sample of the dissolution medium is removed then transferred to a HPLC sample vial and stored in a refrigerator until analysis for estradiol content.

The estradiol content of the sample is quantitated using reverse-phase high performance liquid chromatography (Waters QA-1 Analyzer or other suitable liquid chromatographic system; electronic integrator; column: 15 cm×4.6 mm ID Supelco C-18; mobile phase: 60% water/40% acetonitrile v/v; flow rate: 2.0 mL/min; detector: uv, 280 nm at 0.2 AUFS; chart speed: 0.5 cm/minute; run time: 8 minutes; injection volume: 50 µL).

The percent released is obtained using a software package such as "Dissolution" (available from MIJAC Enterprises) or by use of the following equation:

$$R_i = \frac{[C_i \times (150 - ((i-1) \times 2))] + SUM[(C_{a-1}) \times 2]}{(T.C. \times S.A.)} \times 100$$

where:

$R_i$=percent of estradiol released from the sample at time point "i"
i=sequential number of time point (values: 1, 2, 3, ... t)
$C_i$=sample concentration (µg/mL) from HPLC analysis at time point i
SUM=the summation from a=1 to t
$C_0$=0
T.C.=theoretical estradiol content in µg/cm²
S.A.=surface area of patch sample in cm²

TABLE 1

Release Rate Test Results

| Example | Desiccant | Initial | 1 Month 40° C./ 75% RH | 2 Month 40° C./ 75% RH | 8 Month 40° C./ 75% RH |
|---------|-----------|---------|------------------------|------------------------|------------------------|
| 1 | Yes | 97% | 99% | 98% | 96% |
| C-1 | No | 98% | 92% | 81% | 50% |

TABLE 1-continued

Release Rate Test Results

| Example | Desiccant | Initial | 1 Month 40° C./ 75% RH | 2 Month 40° C./ 75% RH | 8 Month 40° C./ 75% RH |
|---------|-----------|---------|------------------------|------------------------|------------------------|
| 2 | Yes | 92% | 89% | 92% | — |
| C-2 | No | 94% | 69% | 61% | — |
| 3 | Yes | 94% | 97% | 90% | — |
| C-3 | No | 98% | 92% | 77% | — |
| 4 | Yes | 90% | 85% | 88% | — |
| C-4 | No | 105% | 79% | 82% | — |
| 5 | Yes | 95% | 94% | 92% | — |
| C-5 | No | 103% | 87% | 74% | — |

EXAMPLE 6

A Ross Mixer was charged with adhesive copolymer solution [104,721 g of 75/5/20 isooctyl acrylate/acrylamide/vinyl acetate 22.2% solids in 90/10 w/w methanol/ethyl acetate prepared generally as described in U.S. Pat. No. 5,223,261 (Nelson et al.)], estradiol, USP (912 g), glyceryl monolaurate (1,120 g), isopropyl myristate, NF (3,200 g), and ethyl oleate, NF (4,480 g). The mixer lid was damped in place and the ports were sealed to minimize loss of solvent during mixing. The mixer blade was set at a speed of 24 rpm and the contents were mixed for about 19 hours. The resulting formulation was transferred using nitrogen pressure (3–5 psi, 211–351 g/cm²) to polyethylene containers. The formulation was die coated onto a one side silicone coated polyester release liner (2 mil, 0.051 mm). The coated release liner was oven dried at 52° C. for 1.25 minutes, at 107° C. for 1.25 minutes and at 121° C. for 1.25 minutes. This material was then laminated to two side corona treated low density polyethylene film (3 mil, 0.076 mm) to provide rollstock containing 1.6 mg of estradiol per 5.14 cm². A portion of the rollstock was die cut into 5.0 cm² patches. Each patch, along with a desiccant package, was packaged in a heat sealed multilaminate pouch (exterior to interior: polyester film, ethylene copolymer, aluminum foil, adhesive, Barex™ 210 film; available as LCflex 81703 from Smurfit Flexible Packaging, Schaumberg, Ill.). The desiccant package (DesiMax Desiccant Label, Multiform Desiccants, Inc., Buffalo, N.Y.) contained 100 mg of 4 A molecular sieve between a water vapor impermeable styrene/butadiene copolymer film (OPTACITE SQZ, Dow Corning) and a metallized polyethylene terephthalate/paper laminate (Schwartz Paper Company) sealed around their periphery by an adhesive bond and having a pressure sensitive adhesive coated on the exterior surface of the styrene/butadiene copolymer film. The desiccant package was adhered to the interior surface of the pouch.

Comparative Example 6

A portion of the rollstock prepared in Example 6 was die cut into 5 cm² patches. The patches, without a desiccant package, were heat sealed into multilaminate pouches identical to those used in Example 6.

The packaged patches from Example 6 and Comparative Example 6 were stored in a stability chamber at 40° C./75% relative humidity. After 1 week the patches of Comparative Example 6 contained crystals whereas there were no crystals present in the patches of Example 6. After 12 months the results were the same. After 12 months the release rate of estradiol from the patches was determined using the test method described above. The results of the release rate test are shown in Table 2 where each value is the average of determinations for 6 separate patches.

TABLE 2

Release Rate Test Results

| Example | Time (minutes) | % Released |
|---|---|---|
| 6 | 10 | 22.3 |
|   | 45 | 56.8 |
|   | 180 | 88.7 |
| C-6 | 10 | 12.3 |
|   | 45 | 31.8 |
|   | 180 | 50.6 |

EXAMPLE 7

A 5 gallon carboy was charged with adhesive copolymer solution [15,856 g of 75/5/20 isooctyl acrylate/acrylamide/ vinyl acetate 30.0% solids in 90/10 w/w methanol/ethyl acetate prepared generally as described in U.S. Pat. No. 5,223,261 (Nelson et al.)], estradiol, USP (187 g), glyceryl monolaurate (229 g), isopropyl myristate, NF (655 g), and ethyl oleate, NF (917 g). The carboy was capped then placed on a platform shaker for about 26 hours. The formulation was allowed to stand until air bubbles had dissipated. The formulation was die coated onto a one side silicone coated polyester release liner (2 mil, 0.051 mm). The coated release liner was oven dried at 52° C. for 1.25 minutes, at 107° C. for 1.25 minutes and at 121° C. for 1.25 minutes. This material was then laminated to two side corona treated low density polyethylene film (3 mil, 0.076 mm) to provide rollstock containing 3.75 mg of estradiol per 12.5 cm². A portion of the rollstock was converted on a Mark Andy Converter into 12.5 cm² oval patches on octagonal extended releases liners (ScotchPak 9742, available from 3M Company). Each patch, along with a desiccant package, was packaged in a heat sealed multilaminate pouch (exterior to interior: polyester film, ethylene copolymer, aluminum foil, adhesive, Barex™ 210 film; available as LCflex 81703 from Smurfit Flexible Packaging, Schaumberg, Ill.). The desiccant package (DesiMax Desiccant Label, Multiform Desiccants, Inc., Buffalo, N.Y.) contained 100 mg of 4 A molecular sieve between a water vapor impermeable styrene/butadiene copolymer film (OPTACITE SQZ, Dow Corning) and a metallized polyethylene terephthalate/paper laminate (Schwartz Paper Company) sealed around their periphery by an adhesive bond and having a pressure sensitive adhesive coated on the exterior surface of the styrene/butadiene copolymer film. The desiccant package was adhered to the interior surface of the pouch.

Sealed pouches were stored at 4° C., ambient humidity; 30° C., ambient humidity; and 40° C., 75% relative humidity (approximately 100 pouches at each set of conditions). After 4 months and again after 12 months none of the patches showed crystal formation. The release rate of estradiol from the patches was determined using the test method described above. The results are shown in Table 3 below where each entry represents the average of determinations for 6 separate patches.

TABLE 3

Release Rate Test Results

| Storage Conditions | Time (minutes) | % Released |
|---|---|---|
| Initial | 10 | 31.0 |
|   | 45 | 75.5 |
|   | 180 | 97.3 |
| 4 months 4° C./ambient humidity | 10 | 25.9 |
|   | 45 | 66.0 |
|   | 180 | 97.2 |
| 4 months 30° C./ambient humidity | 10 | 26.2 |
|   | 45 | 66.0 |
|   | 180 | 96.2 |
| 4 months 40° C./75% RH | 10 | 27.1 |
|   | 45 | 64.1 |
|   | 180 | 95.1 |

EXAMPLE 8

An experiment was conducted to determine the upper limit of acceptable moisture content in a molecular sieve desiccant package as measured by the Loss on Drying Test Method (described below) by packaging desiccants with varying amounts of moisture with estradiol patches and monitoring the effectiveness of the desiccant in preventing crystallization in the patch.

Desiccant packages (100 mg of 4 A molecular sieve powder in a grease resistant film packet, Multiform Desiccants, Inc., Buffalo, N.Y.) were placed in a 40° C./75% relative humidity stability chamber. One set of 10 packets was pulled at predetermined intervals from the stability chamber. Intervals chosen were 0.5, 1, 2, 3, 4, 24, and 48 hours. This set of ten packets was analyzed for Loss on Drying (LOD) according to the test method described below at each of the intervals. The results are shown in Table 4 below. A second set of desiccant packets was pulled simultaneously with the first set at each of the intervals. This set was packaged with 3 different lots of estradiol patches (details described below).

"Lot 1" patches are 5.0 cm² patches that were die cut from the rollstock prepared in Example 6 above. The patches were cut just prior to use in this experiment.

"Lot 2" patches are 5.0 cm² patches that were die cut from rollstock prepared according to the method of Example 6. The patches were cut just prior to use in this experiment.

"Lot 3" patches were 25.0 cm² patches die cut from rollstock prepared according to the method of Example 6. The patches were die cut then packaged, along with a desiccant packet (100 mg of 4 A molecular sieve powder in a grease resistant film packet, Multiform Desiccants, Inc., Buffalo, N.Y.), in a heat sealed multilaminate pouch (exterior to interior: bleached Kraft paper, low density polyethylene, aluminum foil, low density polyethylene). Approximately 8 weeks later, the patches were removed from the pouches and used in this experiment.

Individual patches, along with a humidity treated desiccant packet, were packaged in a heat sealed multilaminate pouch (exterior to interior: bleached Kraft paper, low density polyethylene, aluminum foil, low density polyethylene). The packaged patches were stored in a stability chamber at 40° C./75% relative humidity. The patches underwent periodic microscopic evaluation for the presence of crystallization. Table 4 below shows the results of evaluation after 28 months on stability. The absence of an entry indicates that no patches were evaluated for that particular set of conditions.

"Controls" were patches packaged without a desiccant packet.

TABLE 4

| Desiccant Pretreatment | | Microscopic Evaluation (28 months) | | |
|---|---|---|---|---|
| Time (hrs) | % LOD | Lot 1 | Lot 2 | Lot 3 |
| 0.5 | 5.4 | No crystals | No crystals | — |
| 1 | 8.9 | No crystals | No crystals | No crystals |
| 2 | 15.3 | Crystals | Mixed[1] | Crystals |
| 3 | 16.4 | — | Crystals | Crystals |
| 4 | 16.0 | — | Crystals | — |
| 24 | 19.1 | Crystals | Crystals | — |
| 48 | 18.6 | Crystals | Crystals | — |
| Controls | — | Crystals | Crystals | Mixed[2] |

[1] One patch had crystals, one did not
[2] One patch had crystals, three did not It is believed that the low level of crystallization seen in the Lot 3 controls is due to the fact that these patches had been packaged with a desiccant prior to their use in this experiment.

Loss On Drying Test Method

A crucible is dried for 3 hours at 425° C. then allowed to cool to room temperature in a desiccator. The crucible is weighed and its weight is recorded as $W_1$. Ten (10) desiccant pouches are cut open and the contents are emptied into the crucible. The crucible containing the desiccant powder is immediately reweighed and its weight is recorded as $W_2$. The crucible and the desiccant powder are dried at 425° C. for 3 hours then allowed to cool to room temperature in a desiccator. The crucible and desiccant powder are weighed and the weight is recorded as $W_3$. The percent loss on drying (% LOD) is then calculated using the following equation:

$$\% LOD = 100 \times \frac{(W_2 - W_1) - (W_3 - W_1)}{(W_2 - W_1)}$$

The claimed invention is:

1. A method of inhibiting precipitation of a drug in the carrier of a transdermal drug delivery device, comprising the steps of:
   (i) providing a non-aqueous carrier comprising a dissolved drug that forms a solid hydrate when exposed to water vapor;
   (ii) providing a desiccant package permeable to water vapor and defining a desiccant compartment containing a desiccant; and
   (iii) placing said desiccant package and said carrier within a substantially sealed water vapor impermeable product package.

2. A method according to claim 1, wherein the desiccant is a synthetic or natural zeolite molecular sieve.

3. A method according to claim 2, wherein the zeolite molecular sieve is selected from the group consisting of 3A, 4A, and 5A molecular sieve.

4. A method according to claim 2, wherein the drug is estradiol.

5. A method according to claim 4, wherein the carrier comprises a pressure sensitive adhesive.

6. A method according to claim 1, wherein the desiccant package is immobilized within the product package.

7. A method according to claim 1, wherein the desiccant package comprises a first base sheet and a first coextensive cover sheet sealed together around their periphery and the product package comprises a second base sheet and a second coextensive cover sheet sealed together around their periphery.

* * * * *